US00PP17171P2

(12) United States Plant Patent
Dirr

(10) Patent No.: US PP17,171 P2
(45) Date of Patent: Oct. 24, 2006

(54) CRAPEMYRTLE PLANT NAMED 'GAMAD III'

(50) Latin Name: ***Lagerstroemia* L.**
Varietal Denomination: Gamad III

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/204,761

(22) Filed: Aug. 16, 2005

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

PP4,185 P * 1/1978 Chopin ..... Plt./252
PP7,968 P * 9/1992 Katsuo ..... Plt./252

* cited by examiner

*Primary Examiner*—Wendy Haas
(74) *Attorney, Agent, or Firm*—Greenlee Winner and Sullivan PC

(57) ABSTRACT

A new and distinct cultivar of crapemyrtle, *Lagerstroemia* L., which is characterized by compact, rounded growth habit; white flowers; bronze foliage that matures to dark green; high mildew resistance.

2 Drawing Sheets

Botanical classification: *Lagerstroemia* L.
Varietal denomination: 'Gamad III'.

BACKGROUND OF THE INVENTION

The present invention relates to a new and distinct cultivar of the ornamental flowering shrub *Lagerstroemia* L., commonly known as crapemyrtle, and hereafter referred to by the varietal denomination 'Gamad III'. The new crapemyrtle originated from open-pollinated seed of 'Gamad V' (U.S. Plant patent application Ser. No. 11/205,282) a compact, pink flowered introduction in 2005 'Gamad III' was selected as a single white-flowered seedling with colorful foliage from 125 seedlings from 'Gamad V' in 1999 by the inventor at Dearing, Ga.

SUMMARY OF THE INVENTION

Plants of the cultivar 'Gamad III' have not been observed under all possible environmental conditions. The phenotype may vary somewhat with variations in environment such as light-intensity, temperature and cultural conditions, however, without any variance in genotype.

The following characteristics have been consistently observed and, to the best knowledge of the inventor, their combination form the unique characteristics of 'Gamad III' as a new and distinct cultivar.

1. Compact, true genetic dwarf.
2. Bronze foliage maturing to dark green.
3. High mildew resistance.
4. White flowers in mid to late summer.

Plants of the new crapemyrtle have been compared to the parent, 'Gamad V'. Comparative evaluations in containers and in the ground at Athens, Ga., showed that 'Gamad III' differed from 'Gamad V' in the following characteristics:

1. Plants of 'Gamad III' produced white flowers compared to the pink flowers of 'Gamad V', and is the only true genetic dwarf white crapemyrtle known to the inventor.
2. Plants of 'Gamad III' had emerging bronze, undulating surfaced foliage which matured to dark green compared to the green foliage of 'Gamad V'.
3. Plants of 'Gamad III' flowered about two weeks later than plants of 'Gamad V'.

Asexual reproduction via tissue culture micropropagation and by traditional vegetative cuttings since 1999 has shown that the unique characteristics of this new crapemyrtle are stable and reproduced true-to-type in successive generations.

BRIEF DESCRIPTION OF THE PHOTOGRAPHS

The accompanying colored photographs illustrate the unique characteristics of the new cultivar, showing the colors as true as it is reasonably possible to obtain in colored reproductions of this type. Colors in the photograph may differ from the color values listed in the detailed botanical description which accurately describe the colors of the new crapemyrtle.

Figure 1:
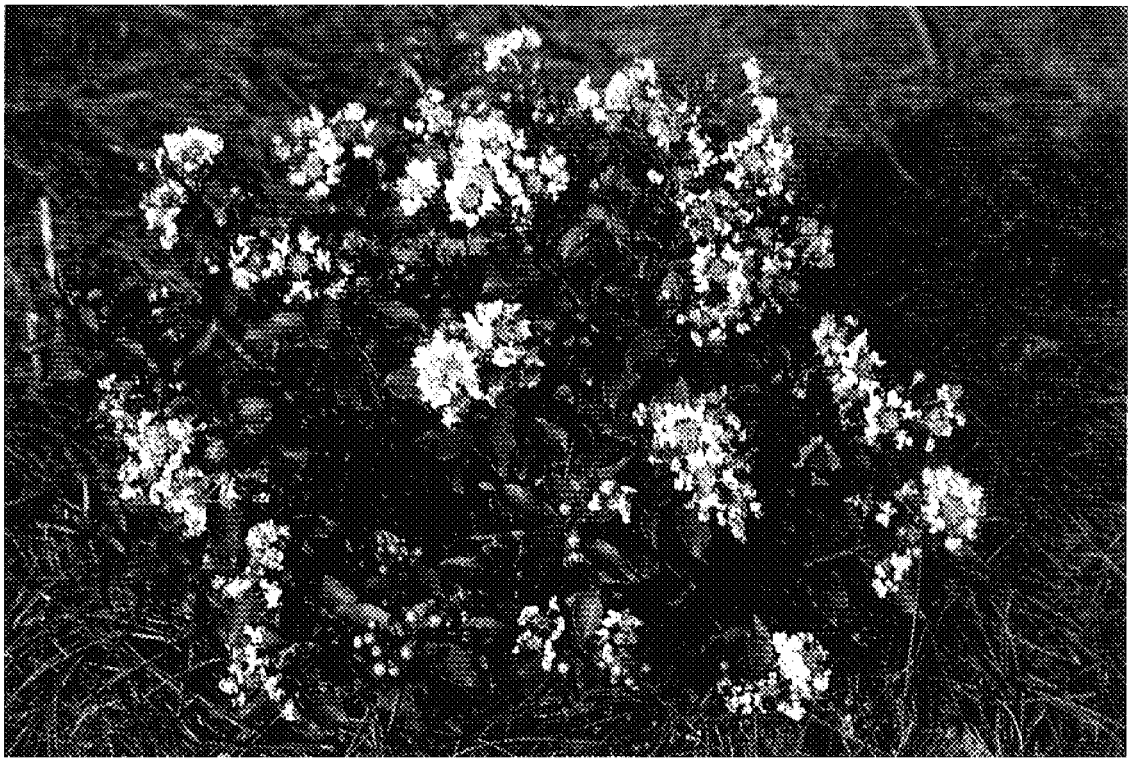

FIG. 1. A one-year-old plant growing in the ground at Chapel Hill, N.C. Picture was taken in August 2004.

Figure 2:
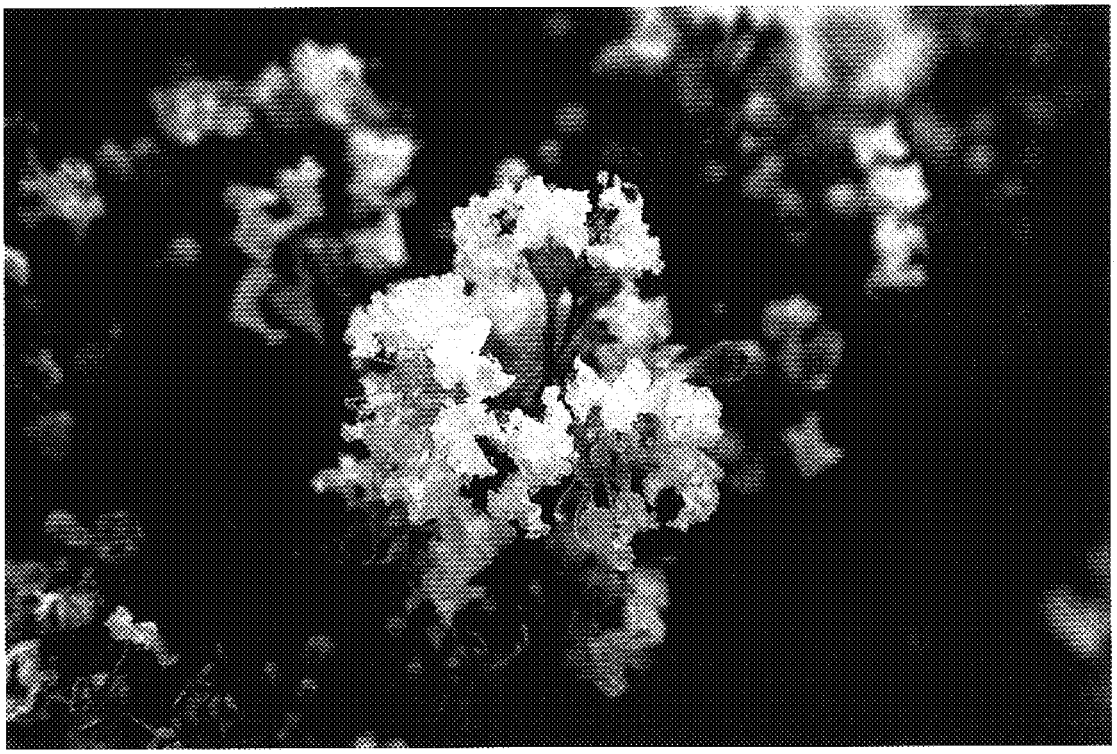

FIG. 2. Flowers of the one-year-old plant showing the long and short stamens present.

DETAILED BOTANICAL DESCRIPTION

The botanical description of 'Gamad III' is based on three-year-old plants, growing in 22 liter containers in an outside nursery research facility in Athens, Ga. (USDA Zone 7b) under conditions which closely approximate commercial production. Measurements are based on the average of 10 to 20 samples, and were taken throughout the main growth period, from March through September in Athens, Ga.

Colors are based on The Royal Horticultural Society Chart, 1995 edition.

The plant has a compact, rounded growth habit with course texture of branching, attaining an average height of 51 cm and width of 64 cm.

First year stems are square and winged, 0.5 mm across, with average internode length of 7.8 mm. They are Greyed-Orange, 164A in color, and there is no exfoliation.

Second year stems are oval, 1 mm across without wings, with color Greyed-Brown N 199A, exfoliating to Greyed-White 156A.

Mature stems are up to 13 mm in diameter, exfoliating and Greyed-White 156A to Orange-White 159A in color.

The vegetative buds are opposite to sub-opposite in arrangement, imbricate, conical in shape, 1 mm in length and 1 mm in width, with no pubescence, and the bud scales are Greyed-Brown 166B in color.

The mature leaf, measured in the middle section of first year stems, averages 43 mm in length and 15 mm in width.

The leaf is linear-elliptical, with an acute apex, cuneate base and entire, undulating margin. The emerging leaf (April in Athens, Ga.) is Greyed-Orange 175A on both upper and lower surfaces with a Greyed-Purple 183A margin. In summer (August), the upper surface is Green 139A and the lower surface is Yellow-Green 146A.

The leaves are arranged opposite to sub-opposite on the stem, are thick, up to 0.5 mm, and have very shiny upper and lower surfaces. The venation is pinnate and the vein color is Greyed-Purple 187A. The petiole is 2 mm in length and 1 mm in diameter, oval in cross-section shape with no pubescence and Greyed-Purple 187A in color.

The flower buds are 7 mm in length and 5 mm in width, with no pubescence, and are Yellow-Green 144B, maturing to Yellow-Green 145A in color.

The flowering period is from late July to September in Athens, Ga.

The inflorescence averages 7.2 cm in length and 6.0 cm in width, and a plant in a 11.8 liter container carries 20 to 30 inflorescences. The color at emergence and in full bloom is White 155D, fading to Red-Purple 65D. There are 20 to 30 flowers per inflorescence. The individual flower averages 16 mm by 24 mm. The peduncle is finely pubescent and is Greyed-Purple 183C in color.

The petals, 5 to 6 per flower, average 11 mm in length by 8.5 mm in width, are fan-shaped with a ruffled, rounded apex, sagittate base and ruffled margin. There is no pubescence. The color of both upper and lower surfaces at peak of bloom is White 155D.

The petal stalk averages 4.8 mm in length and is White N 155C.

The calyx is colored Yellow-Green 145A outside, and Yellow-Green 148A inside.

The pedicel averages 7 mm in length, with no pubescence and is Yellow-Green 144A in color.

The cluster of stamens has a group of short stamens in the center averaging 29 in number, and Yellow-Orange 17B in color. The filament averages 8.9 mm and is Yellow-White 158C in color. There are six longer stamens around the outside of the cluster, Greyed-Orange 163B in color. The filaments average 14.7 mm in length and are colored Red-Purple 163D.

The superior pistil is 20 to 25 mm in length. The stigma is round in shape, and 1 mm across, with no pubescence and Yellow-Green 148A in color. The style is 13.5 mm in length, round in shape, and Greyed-Red 181D in color, with no pubescence. There is a single ovary, 2 mm in diameter, Greyed-Yellow 160A in color.

The mature fruit is a six-valved dehiscent, broad ellipsoidal capsule, measuring 6 to 8 mm in length and 6 to 8 mm in width, prior to dehiscence. The color is Brown 200A. There are multiple seeds per capsule, averaging 6 mm long, and 3 mm wide, with a membranous wing. The color of the seed is Brown 200A, and the wing is Grey-Brown 199D.

I claim:

1. A new and distinct cultivar of crapemyrtle plant named 'Gamad III', substantially as illustrated and described.

* * * * *